United States Patent [19]

Blake et al.

[11] Patent Number: 4,742,011
[45] Date of Patent: May 3, 1988

[54] DEVICES FOR CARRYING OUT CHEMICAL AND CLINICAL TESTS, AND THEIR USE

[75] Inventors: Anthony Blake, Huntingdon; John Coley, Kettering; Ronald Smith, Rushden, all of England

[73] Assignee: Unilever Patent Holdings B.V., London, England

[21] Appl. No.: 740,918

[22] PCT Filed: Mar. 15, 1985

[86] PCT No.: PCT/GB85/00102

§ 371 Date: May 30, 1985

§ 102(e) Date: May 30, 1985

[87] PCT Pub. No.: WO85/04255

PCT Pub. Date: Sep. 26, 1985

[30] Foreign Application Priority Data

Mar. 15, 1984 [GB] United Kingdom ............... 8406752

[51] Int. Cl.$^4$ ............... G01N 33/543; G01N 33/76; B01L 3/00; B01L 9/00

[52] U.S. Cl. ............................ 436/518; 422/58; 422/61; 422/69; 422/102; 422/107; 436/510; 436/807; 436/810; 436/818

[58] Field of Search ............... 422/55, 57, 58, 61, 422/69, 71, 102, 104; 436/810, 807, 510, 518, 818; 211/74; 248/500

[56] References Cited

U.S. PATENT DOCUMENTS

| 1,761,218 | 6/1930 | Lundy et al. | 211/74 X |
| 1,925,540 | 9/1933 | Neuschotz | 211/74 X |
| 3,865,552 | 2/1975 | Marston | 436/810 X |
| 4,008,810 | 2/1977 | Merz | 211/74 X |
| 4,133,466 | 1/1979 | Rosen | 248/500 X |
| 4,147,752 | 4/1979 | Suovaniemi et al. | 422/57 |
| 4,425,320 | 1/1984 | Perry et al. | 436/810 X |
| 4,427,634 | 1/1984 | Truglio | 422/102 X |
| 4,495,151 | 1/1985 | Ohyama et al. | 422/102 |

FOREIGN PATENT DOCUMENTS

| 0010456 | 4/1980 | European Pat. Off. |
| 0014799 | 9/1980 | European Pat. Off. |
| 0031993 | 7/1981 | European Pat. Off. |
| 0042755 | 12/1981 | European Pat. Off. |
| 2314486 | 1/1977 | France |
| 2394086 | 1/1979 | France |
| 2516654 | 5/1983 | France |
| WO82/00058 | 1/1982 | PCT Int'l Appl. |
| 1414479 | 11/1975 | United Kingdom |
| 1511607 | 5/1978 | United Kingdom |
| 1537537 | 12/1978 | United Kingdom |
| 2012955 | 8/1979 | United Kingdom |
| 2015158 | 9/1979 | United Kingdom |
| 1571782 | 7/1980 | United Kingdom |
| 1584129 | 2/1981 | United Kingdom |

Primary Examiner—Michael S. Marcus
Attorney, Agent, or Firm—Cushman, Darby & Cushman

[57] ABSTRACT

A device for carrying out chemical or clinical testing of a liquid sample, for example a urine sample, by a specific binding assay, said device comprising a test component (2) which has a sensitized solid surface (2a) carrying an immobilized component of a specific binding pair relevant to the assay, and a handling piece (1), and characterized in that the test component (2) bearing the sensitized surface (2a) is removably mounted in spaced relationship with a removably mounted accessory component (4) carrying an accessory solid surface (5), and in that there is a space (4a) between the sensitized surface (2a) and the removable accessory component (4) to act as a container for sample liquid, so that when the device is contacted with a sample liquid source or immersed in liquid which is to provide the test sample, liquid of the sample can enter the space (4a) to contact the sensitized surface (2a), and the accessory surface (5) acts to retain and contain sample liquid in contact with the sensitized surface (2a) even after removal of the device from further contact with or immersion in the source of sample liquid, and in that the test component (2) is so formed that after removal of the removable accessory component (4) the sensitized surface (2a) is left exposed and accessible to further treatment liquid such as washing liquid and/or reagents.

16 Claims, 2 Drawing Sheets

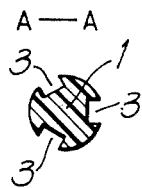
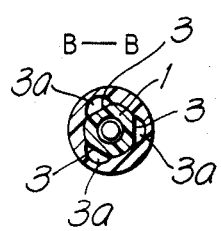
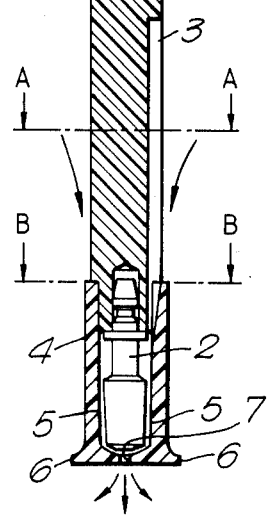
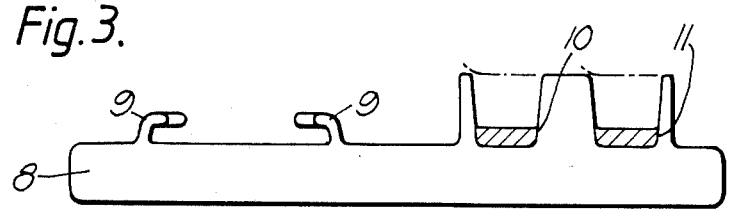

DEVICES FOR CARRYING OUT CHEMICAL AND CLINICAL TESTS, AND THEIR USE

This invention relates to devices for chemical and clinical testing, and their use. It particularly concerns improved apparatus for carrying out such tests. The devices of the invention are applicable to a well-known range of tests, which range is wide and not particularly limited by the function or chemical basis of the tests: it especially includes the known specific binding or specific affinity tests, for example immunologically-based methods of detection such as immunoassays: (all such immunological and other specific binding methods are generically referred to in this specification as immunoassays). The literature of specific binding assays reviewed in European Specification No. 0 014 530 is representative of known kinds of such assays.

A large range of apparatus types has been devised to carry out immunoassays and other clinical tests: in nearly every case the test procedure demands the interaction of a plurality of reactants and a corresponding large number of manipulations is required on the part of the user. The range of apparatus already known includes tubes, beads, slides, and tube inserts coated with sensitising material for the purposes of the tests, and proposals have also been made to use sensitised brushes or bodies with a convoluted surface to carry sensitising material, e.g. immunosorbent material, such as for example antibody, antigen or specific binding partners for either of them.

It is an aim of this invention to simplify the handling of such tests. It is also an aim of this invention to provide apparatus for clinical immunological testing which is simple and convenient to use in an environment far removed from a specialist immunological testing laboratory, e.g. at a patient's bedside or at home.

A further aim of the invention lies in providing a construction of apparatus for simplified clinical and chemical testing involving a sensitised carrier body which facilitates uniform production of such a sensitised body as well as its convenient handling in use.

According to the invention, an apparatus for carrying out a test or assay of any of the kinds described above, using a liquid sample possibly containing some quantity of an analyte to be tested for, includes a sensitised solid surface and is improved in the following way: the test component which includes the sensitised solid surface is removably mounted in spaced relationship with an accessory solid surface carried on an accessory body, so that upon contact with or immersion in liquid which is to provide the test sample, liquid of the sample contacts the sensitised solid surface, and the accessory solid surface acts to retain sample liquid (in some embodiments, possibly a definite, consistent, and maybe standardised volume of sample liquid) in contact with the sensitised solid surface after any removal of the apparatus from further contact with or immersion in the liquid. In certain embodiments, the accessory solid surface can be closely spaced from the sensitised surface, and may be so placed that it helps in conducting a flow of sample liquid over the sensitised solid surface, e.g. by capillary action or other effect of surface tension. In other embodiments, the accessory solid surface can take the form of a sample liquid holder such as a cup, which is removably fitted to the test component or to the handle. In use, the test component is later removed from its association with the accessory solid surface, and can be treated further, e.g. by washing and exposure to further reactant.

The description given hereinbelow gives forms and examples of the improved devices according to the invention, for carrying out chemical or clinical testing of liquid samples, for example urine samples, by specific binding assay, such a device comprising a test component (2) which has a sensitised solid surface (2a) carrying an immobilised component of a specific binding pair relevant to the assay, and a handling piece (1), and in which the improvement comprises a removably mounted accessory component (4) carrying an accessory solid surface (5), which is removably mounted in spaced relationship with the test component (2) bearing the sensitised surface (2a), whereby there is left a space (4a) between the sensitised surface and the removable accessory component (4) to act as a container for sample liquid, so that when the device is contacted with a sample liquid source or immersed in liquid which is to provide the test sample, liquid of the sample can enter the space (4a) to contact the sensitised surface (2a), and the accessory surface (5) acts to retain and contain sample liquid in contact with the sensitised surface (2a) even after removal of the device from further contact with or immersion in the source of sample liquid, the test component (2) being so formed that after removal of the removable accessory component (4) the sensitised surface (2a) is left exposed and accessible to further treatment liquid such as washing liquid and/or reagents. The numerals given in the above statement are intended only for purposes of illustration and explanation but not of limitation, and refer to particular examples of the device as given below and illustrated in the accompanying drawings.

A prior art search based on the subject matter of the present invention has disclosed the existence of the following references:

GB Pat. No. 2 012 955 (Abbott) describes for example an immunotest device comprising an open tube with an immunosensitised bead trapped within, intended to allow decantation of liquid without losing the bead.

GB Pat. No. 1 537 537 (American Home Products) describes for example a testing device for detecting or measuring HCG in serum or urine: the device calls for sample liquid to be added to a device comprising a receptacle and an insert: the insert comprises an arrangement of semipermeable membrane and absorbent and is intended to reduce the bulk of the sample liquid by ultrafiltration, while leaving the analyte outside the membrane in concentrated form, to react later with an agglutination/inhibition reagent in the base of the receptacle after removal of the insert.

GB Pat. No. 1 511 607 (ICL/Scientific) describes for example a urine test device comprising a tube and an aspirator that fits within the tube, intended to suck up the lower part of a liquid sample contained in the tube, possibly together with any particles in the liquid sample that may have sedimented to the bottom of the tube.

GB Pat. No. 2 015 158 (Reijo Vihko) shows for example discardable immunotest apparatus with a series of detachable connected parts, each carrying antibodies on its surface for reaction with each of several antigens. The detachable parts can be interlocking tubes, and there is mention by way of alternative of parts disposed one within another and facing one another to define a reaction space between them.

GB Pat. No 1 584 129 (Piasio et al) shows for example an immunotest arrangement with a receptacle and an immunologically sensitised solid insert with a handle and a plurality of elements, eg fins, attached to the handle.

GB Pat. No. 1 571 782 (Finn-Pipette Osmo) shows for example annular solid immunologically sensitised inserts for immunotest reaction vessels, to allow measurement light for photometry of the reaction solution to pass through the holes in the annuli.

GB Pat. No. 1 414 479 (Abbott) shows for example immunologically sensitised solids provided with handles and made in the shapes of inter alia hemispherical, conical and cruciform inserts for immunotest reaction containers, together with reaction containers of complementary shape, eg hemispherical or conical.

EP Pat. No. 0 042 755 (Unilever) shows for example interfitted sticks or rods with immunosorbent surfaces carried in multiple on handling-pieces and for insertion into immunotest reaction vessels.

EP Pat. No. 0 031 993 (Ventrex) shows for example an immunotest apparatus with a sensitised "fin-stick" (a rod carrier to which a number of immunologically sensitised vanes is attached) retained within an immunotest reaction tube.

EP Pat. No. 0 014 797 (Eastman Kodak) shows for example a liquid-spreading device with opposed plates bearing crossed microgrooves.

EP Pat No.0 010 456 (Eastman Kodak) shows for example a liquid transport device with an aperture to a receptacle having interior corners, eg a hexagonal inlet aperture.

Also in the prior art are microdiluters for laboratory use, comprising handles with multi-prong ends to pick up desired volumes of liquid and hold them mostly by capillary action before they are transferred and dispensed into larger liquid volumes.

Also in the prior art are numerous liquid sample collection and testing devices including urine collection and testing devices, based on cups or tubes or dropper tubes or reagent strips to be wetted with the sample liquids.

Several of the prior art arrangements above, though intended for immunotests, have not been designed with a view to easy handling of body fluid samples such as urine samples.

Considered from the point of view of those users of such tests who may not be skilled in the art of handling and measuring liquid volumes as in a laboratory, we believe the arrangements of the prior art, including those intended for application to body fluid collection and testing, are generally somewhat messy and awkward to use, or at least to use with a degree of accuracy needed for satisfactory execution of the tests to be performed with their aid.

It is an aim of the invention to provide greater convenience of handling in connection with such liquid collection and diagnostic test procedures.

Particular embodiments of the devices of the invention are given by way of example without limitation as follows:

(a) The test component carrying the sensitised solid surface can be a slip, plate, bead, peg or section of hollow body such as tubing, mounted on a handle or other holder.

(b) The accessory solid surface can be of substantially complementary shape to the sensitised solid surface and be removably fixed at a location close to but spaced slightly apart from the sensitised surface; it can be a surface of e.g. a shroud, mesh, cover or plug.

(c) The accessory body can be for example a removable snap-on/snap-off fitment or a frictional sliding fitment on the handle or holder, or on the test component carrying the sensitised solid surface. If desired, the handle or holder can have an ejection device which the user can manipulate to dislodge or demount the accessory body when desired.

In one form of device according to the invention, the accessory body can comprise a body of absorbent liquid-retentive material such as a sponge, to hold sample liquid in contact with the sensitised surface of the test component.

When the test component carrying the sensitised solid surface is fitted to the accessory body carrying the accessory solid surface, they cooperate in such a way that passage is left for entry of sample liquid into the space between the sensitised surface and the accessory surface. Passages can be formed according to convenience either within the handle, within the accessory body carrying the accessory surface, or within the test component, or at the places where any two of these three contact each other. The location of such passage can be chosen at will according to the particular shapes chosen for the rest of the apparatus.

Preferably there is also another passageway provided for air to escape from the surfaces between which the sample liquid is to enter, but the need for this depends on the overall form of the apparatus and passage for liquid entry.

(d) The test component can be removed from its mounting in association with the accessory body, with its accessory solid surface, by pulling off the snap-off or frictional sliding fitment. This can most conveniently be done if the accessory body possesses (in addition to its means for removable connection to the test component carrying the sensitised solid surface) means for attachment to a test kit base or other component which can be handled easily and used to detach the accessory body from its fitted position in proximity to the test component.

It can be especially convenient and desirable to provide the test component carrying the sensitised solid surface as a plug-in fitment to a handle: the test component may be either detachable from the handle or not. Then the test component can be mass-produced to ensure uniformity, without involvement of the handle piece in the manufacturing conditions.

In one type of embodiment of the invention which can centre around a sensitised component plug-fitted to a handling-piece, the accessory surface can be that of a sample holder which functions as a cup to hold sample liquid around the sensitised surface of the test component.

The sample holder can have formations (e.g. vanes) allowing it to be push-fitted on to the sensitised component and/or handle. The holder can also be arranged for positive location on a stand or in a further container or handling piece. Then the steps needed to use the device are (a) fill the holder with sample liquid enough to contact the sensitised surface, (b) leave in contact long enough for the needs of the particular test in view, (c) engage the holder with the stand or further container or handling piece, (or otherwise eject or dispose of the sample-liquid holder and its contents), so as (d) to obtain the handle and test component free of the other parts of the apparatus so far used, and (e) then to subject the test component to any further procedures needed by the particular test in view.

It will often be convenient to incorporate the stand or further container or handling piece (or other means to separate the test component from the component carrying the accessory solid surface) as part of the packaging or casing in which the test apparatus is supplied to the user, e.g. as part of the lid or base of such a casing.

Where the test to be carried out requires accessory reagents, some or all of these can if desired be deposited on the surface of the accessory body in proximity to the sensitised surface of the test component. For example, an immunoassay apparatus according to the invention may call for an immunosorbent sensitisation of the test component surface: and in the event that a labelled immunological material is also involved in the test reaction, such a material (e.g. an enzyme-labelled antigen, hapten or antibody) can be carried on the accessory solid surface, e.g. in a form which is releasable into the sample liquid layer held between the test component and the accessory solid surface, such as a dry layer, e.g. a sucrose glaze, or a thin film layer based on gelatin or other film-former such as polyvinyl alcohol. The formation of such layers and glazes is well known in itself and in itself does not constitute this invention. In this case, it will usually be desirable and even necessary for the volume of sample liquid retained between the accessory surface and sensitised test component surface to be consistent and standardised, as can be achieved by the use of examples as illustrated below.

Most usually, the sensitised surface of the test component of the apparatus described herein is sensitised by immobilising an antibody or antigen or other component of a specific binding reaction to the surface, in a known manner. Such immobilisation methods are now well known and widespread in the literature and in themselves do not constitute the present invention. One preferred method is to adsorb the antibody to a polystyrene surface in a known manner. Other suitable methods are described and cited in European Specification No. 0 014 530, especially the glutaraldehyde method and the methods described in U.S. Pat. No. 3 817 837 (cols 31–34), and GB Specification Nos. 1 316 990 and 1 485 122–3.

Suitable examples of glutaraldehyde coupling techniques have been available in the literature for a long time, in for example S Avrameas, (1969) Immunochem 6 pp 43 et seq, and in "The Enzyme Linked Immunosorbent Assay (ELISA)" by A. Voller, D. F. Bidwell and A. Bartlett, (1979) (published by Dynatech Europe, Guernsey, ISBN 0.906036.01.1).

Since at present the most wanted application of the devices of the present invention appears to be for the purpose of pregnancy testing by analysis of female (especially, but not exclusively, human) urine samples, a corresponding suitable material to fix on to the test component surface is antibody to human chorionic gonadotrophin (HCG). Other antibodies which are suitable coupling partners for the purposes of tests of related diagnostic significance are for example anti-luteinising hormone (anti-LH) and anti-prolactin. Antigens and haptens are further suitable examples of coupling partners, especially HCG itself.

The chemical reaction schemes of the assays which are carried out by the help of the devices of the present invention do not in themselves constitute or limit this invention. It can be mentioned, however, that any of the known specific binding assay reaction formats, such as a competitive assay, sandwich assay, immunometric assay, or antiglobulin assay, among others, can be carried out by suitable choice and arrangement of known reagents in known manner. Representative literature about the occurrence of urinary analytes related to pregnancy and fertility is given in for example U.S. Pat. No. 4 016 250 and 4 094 963. The use of the devices of the present invention is not however limited to any one example of an immunoassay or diagnostic assay.

EXAMPLE AND DRAWINGS

The following description gives examples of apparatus of the invention and explains its use by reference to test reagents and preparative conditions which are substantially conventional and of well-known kind, chosen for illustration, which in themselves do not constitute the present invention.

FIGS. 1, 2A and 2B of the accompanying drawings show a diagrammatic part-section through an embodiment of apparatus in accordance with the invention, together with auxilliary cross-sections through lines A—A and B—B in the main section.

FIG. 3 shows in diagrammatic part cross-section a base unit for use with the device of FIGS. 1, 2A and 2B.

Figure 4:
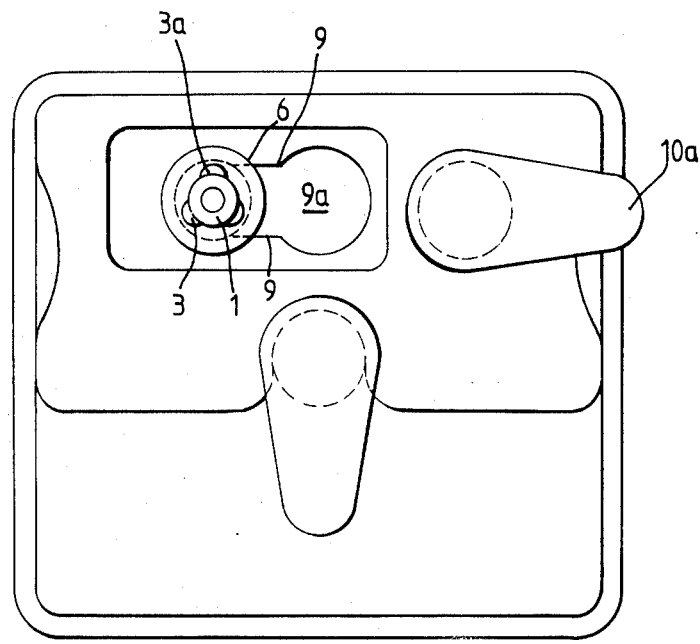
FIGS. 4–6 show in diagrammatic plan cross-section and elevation a further form of the apparatus.

Shown in the diagrammatic part-sectional drawings is an apparatus for carrying out immunological tests comprising a handle 1 of plastics material. Into a recess in the lower end of handle 1 is plugged in a polystyrene or nylon peg 2 which has been sensitised in known manner with a high-affinity anti-HCG antibody, reacted with the plastics surface in sensitising treatment liquid under sensitising conditions (e.g. those appropriate to a known adsorption or glutaraldehyde method) at a concentration of about 2 micrograms/milliliter. The part of the peg 2 having a sensitised surface 2a is of the order of 5 millimeter long in a suitable embodiment of this example. Techniques for preparation of immunosorbents are well known in themselves and need be no further described to enable the skilled reader to carry out this invention.

Handle 1 also has a number of longitudinal grooves 3 therein, to allow passage of sample liquid towards the sensitised part of peg 2. As a frictional sliding fit over the end of handle 1 and over peg 2 there is provided a perforated plastics shroud 4 of which the internal surfaces 5 are substantially complementary in shape to the overall shape of sensitised surfaces of the peg 2. Shroud 4 also in this embodiment has grooves 3a complementary to grooves 3 to allow passage of sample fluid into the centre space within shroud 4. There is no need however for any grooves or the like which may be present on the sensitised part of the peg 2 to be repeated in the surface 5. The space 4a within shroud 4 between surface 5 and surface 2a of peg 2 may be such as to allow of the order of 50 microliter of liquid, (e.g. up to 100 microliter) to be held between them. Using these dimensions, this can easily be arranged to be a defined or standard volume of liquid taken up automatically and regulated by surface tension/capillarity when the device is used.

Shroud 4 also carries flanges 6 which allow it to be positively located and locked in place on a holder base (8). Shroud 4 also has a lower perforation 7 to allow escape of air when the assembly of handle 1, peg 2 and shroud 4 is exposed to sample liquid, and sample liquid enters via grooves 3 and 3a to contact peg 2 and surfaces 5. Holder base 8 has flange formations 9 which together with the rest of base 8 form a groove or grooves by which to interlock with and hold shroud 4 as a sliding fit by its flanges 6. Base 8 also has two or more reagent wells 10 and 11 fitted with removable seals to contain reagents to carry out the test.

In use, the assembly comprising handle 1, peg 2 and shroud 4 is exposed to and contacted with a source of liquid to provide a sample. This may be a sample of serum, or urine, e.g. the lower end of the assembly may be held in a urine stream of a person to be the subject of the test, to collect a sample, which enters into space 4a between the sensitised surface 2a and accessory component 4.

After sample collection, the assembly may be removed from the source and slotted into flanges 9 by means of flanges 6 so that it is held in holder base 8, and allowed to stand to incubate for a specified time chosen to suit the particular reagents involved, so that the sample liquid reacts with the specific binding agent carried by surface 2a. Then the user may pull handle 1 and peg 2 away from the holder, separating test component 2 from accessory component 4, leaving shroud 4 behind. The user can then wash the peg 2 in water or other wash fluid if so instructed according to the nature of the particular test, which in itself does not constitute this invention, and dip the peg successively for specified times (which may be for example of the order of 5-30 minutes per reaction step) with intermediate washes, into reagent wells 10 and/or 11 successively. In the present example, when applied to a test for HCG, the well 10 may be provided with a liquid having a content of HCG conjugated with alkaline phosphatase, (e.g. at 0.2 microgram/milliliter) and a tear-off sealing foil cover, and well 11 may be provided with a liquid having a content of (e.g. 1 mg/ml) bromochloroindolylphosphate (substrate reactable with alkaline phosphatase to yield blue product, under known suitable conditions). According to the content of HCG in the original sample, the liquid in well 11 either develops or fails to develop a blue coloration after incubation. This can be visualised by a colour comparison chart, if desired in the presence of a (possibly inert) background colour (e.g. yellow) to convert the colour development into a change of hue, e.g. from yellow to green. The reagents mentioned hereinabove are all well known per se.

In an alternative embodiment the conjugate with alkaline phosphatase (or other enzyme, such as peroxidase) can be supplied instead as a releasable dried layer on surface 5 of accessory component 4, as mentioned above.

By suitable choice of known colour-forming reaction, in alternative embodiments, the colour can be made to develop in liquid form or on the sensitised surface itself. Any suitable known enzyme or colour-developing reaction can be used in connection with the tests which are carried out by the aid of the devices of the present invention.

The invention described herein comprises any and all combinations of the features and steps set out above, and the skilled reader will appreciate that the invention includes a wide variety of modifications based upon such disclosure.

A further and preferred variant embodiment of the invention is illustrated with reference to further accompanying drawing FIGS. 4, 5 and 6.

These figures respectively show a diagrammatic and part-sectional plan, cross-section on line AA in the plan, and side elevation towards AA of a sampling and testing apparatus according to this further embodiment.

In these drawings, similar numbers to the numbers shown in FIGS. 1-3 indicate functionally similar parts comparable with the parts indicated in the earlier drawings.

Figure 5:
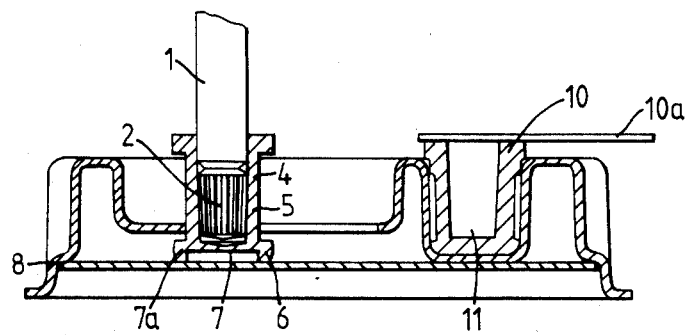
Figure 6:
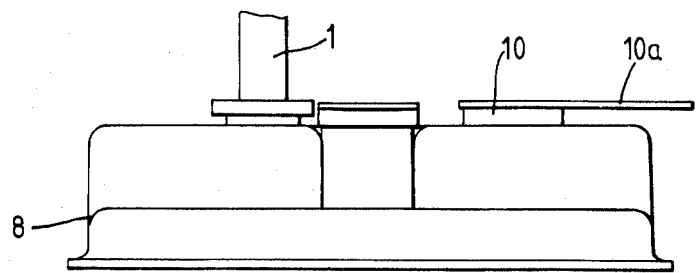

In this embodiment, referring to shroud 4 shown in section in FIG. 5, a downwardly extending rim 7a is provided so that when the sampling handle and shroud are placed vertically on a flat surface, the surface does not interact with any liquid meniscus located in passageway 7 after a liquid sample has been collected. Passageway 7 is in this embodiment less than about 0.5-0.6 mm, e.g. about 0.3 mm in diameter, and the peg 2 and shroud 4 are dimensional substantially as described in connection with the earlier drawings.

The base-unit of this further embodiment shows a modified layout (FIG. 4), and in particular a double-socket compartment 9a into which the shroud 4 can be plugged, and moved to one side (left as seen in the drawing), to enable the handle and peg to be pulled free when flanges 9 have engaged with the complementary rim 6 on shroud 4.

It will be understood that any of the features of this further embodiment can be modified and combined with the foregoing description.

We claim:

1. A sample collecting and testing device comprising:
   (a) a test component having a test component surface, said test component surface being sensitized with an immobilized component of a specific binding pair relevant to said assay;
   (b) a handling-piece connected to said test component;
   (c) an accessory component having an accessory solid surface which is of substantially complementary shape to said test component surface and removably fixed in slightly spaced apart relationship therewith, to define therebetween a containing space for retaining a liquid sample;
   (d) a means for removably fixing said accessory component (c) to said handling-piece (b) or to said test component (a) so that said accessory component (c) is maintained in said slightly spaced apart relationship with said test component (a) and so that said accessory component (c) remains fixed to said handling-piece (b) or said test component (a) when said device is held and moved by said handling-piece (b); and
   (e) at least one aperture through which a sample of liquid from an external source enters said space when said device is held in contact with said source, said sample being retained in contact with said test component surface, said device further comprising:
   (f) a support component, and
   (g) a means for interlocking said support component (f) with said accessory component (c) to facilitate removal of said test component (a) from said accessory component (c) without the user handling either said test component (a) or said accessory component (c) directly.

2. A sample collecting and testing device according to claim 1, further comprising an aperture in said accessory component (c) through which air escapes from said space when said device is used to collect a sample.

3. A sample collecting and testing device according to claim 1, wherein said space between said test component surface and said accessory component is narrow enough to retain sample liquid by capillarity or surface tension.

4. A sample collecting and testing device according to claim 1, wherein said means (d) comprises surfaces providing a removable frictional sliding fit of accessory component (c) on test component (a) or handling-piece (b), with at least one aperture (e) located between said test component (a) or handling-piece (b) and said accessory component (c).

5. A sample collecting and testing device according to claim 1, wherein said support (f) further comprises a base unit comprising at least one liquid reaction well for containing a reagent for said assay.

6. A sample collecting and testing device according to claim 1, wherein said accessory component (c) is formed to provide a sample liquid holder in the form of a cup which is removably fixed to test component (a) or handling-piece (b).

7. A sample collecting and testing device according to claim 1, wherein said accessory solid surface carries a releaseable reagent which disperses into said sample of liquid during use of said device.

8. A sample collecting and testing device according to claim 1, wherein said test component (a) is sensitized with an immobilized analogue or binding partner of a specific binding pair involving human chorionic gonadotrophin.

9. A process for sampling a liquid and testing said sample by a specific binding assay, comprising the steps of:

(i) contacting a test device with a source of liquid to be sampled, said test device comprising (a) a test component having a test component surface, said test component surface being sensitized with an immobilized component of a specific binding pair relevant to said assay, (b) a handling-piece connected to said test component, (c) an accessory component having an accessory solid surface which is of substantially complementary shape to said test component surface and removably fixed in slightly spaced apart relationship therewith, to define therebetween a containing space for retaining a liquid sample, (d) a means for removably fixing said accessory component (c) to said handling-piece (b) or to said test component (a) so that said accessory component (c) is maintained in said slightly spaced apart relationship with said test component (a) and so that said accessory component (c) remains fixed to said handling-piece (b) or said test component (a) when said device is held and moved by said handling-piece (b), and (e) at least one aperture through which a sample of liquid from an external source enters said space when said device is held in contact with said source, said sample being retained in contact with said test component surface; and (ii) removing said test device from further contact with said source of liquid, and allowing said accessory surface to retain and contain sample liquid in contact with said sensitized surface; and (iii) separating said removably fixed accessory component from said test component to expose said test component surface, said process further comprising the steps of interlocking said accessory component and a base unit, which base unit is a support component for said test device;

allowing said test device supported by said base unit to stand for a predetermined time; and removing said test component from said accessory component so that direct manual handling of said sensitized surface or said accessory component does not occur.

10. A process according to claim 9, wherein said process further comprises the step of transferring said test component into at least one liquid reaction well formed on said base unit, which reaction well contains a liquid reagent for said assay.

11. A process according to claim 9, wherein said accessory component comprises a perforated or apertured removable shroud or cover closely spaced a short distance from said test component surface and removably fixed to said test component or to said handling piece.

12. A process according to claim 9, wherein said removably fixed accessory component is frictionally fitted on said test component or said handling piece, and wherein said accessory component and said test component or said handling piece are formed so that there is at least one aperture between said test component or said handling piece and said accessory component through which a sample liquid enters said space therebetween.

13. A process according to claim 9, wherein said space between said accessory surface and said test component surface is narrow enough to retain sample liquid by capillarity or surface tension.

14. A process according to claim 9, wherein said accessory component further comprises an aperture through which air escapes from said space.

15. A process according to claim 9, comprising the step of allowing a releasable reagent carried on said accessory component surface to disperse in said sample liquid before removing said accessory component.

16. A process according to claim 9, wherein said immobilized component of said specific binding pair is selected from the group consisting of specific binding analogues and binding partners of human chorionic gonadotrophin.

* * * * *